United States Patent
Kawai et al.

(10) Patent No.: US 7,175,991 B2
(45) Date of Patent: Feb. 13, 2007

(54) METHOD OF MEASURING BINDING SITE ON PLASMA PROTEIN OF PLASMA PROTEIN-BINDING DRUG AND METHOD OF MEASURING PLASMA PROTEIN MUTATION

(75) Inventors: Keiichi Kawai, Kanazawa (JP); Norito Takamura, Nobeoka (JP)

(73) Assignee: Nihon Medi-Physics Co., Ltd., Hyogo-ken (JP)

( * ) Notice: Subject to any disclaimer, the term of this patent is extended or adjusted under 35 U.S.C. 154(b) by 0 days.

(21) Appl. No.: 10/532,819

(22) PCT Filed: Oct. 23, 2003

(86) PCT No.: PCT/JP03/13572

§ 371 (c)(1),
(2), (4) Date: Apr. 26, 2005

(87) PCT Pub. No.: WO2004/040309

PCT Pub. Date: May 13, 2004

(65) Prior Publication Data

US 2006/0166269 A1   Jul. 27, 2006

(30) Foreign Application Priority Data

Oct. 31, 2002   (JP)   .............................. 2002-317568

(51) Int. Cl.
*G01N 33/68*   (2006.01)

(52) U.S. Cl. ........................................................ 435/7.1
(58) Field of Classification Search ..................... None
See application file for complete search history.

(56) References Cited

FOREIGN PATENT DOCUMENTS

WO   WO 00/78352 A   12/2000

OTHER PUBLICATIONS

Pritchard et al., Plasma Protein Binding of Bepridil, J Clin Pharmacol, 1985, 25, pp. 347-353.*
Kawai, et al. "Competitive displacement of 99mTc-MAG3 serum protein binding in in-vitro and in-vivo", *J. Labelled Cpd. Radiopharm.* vol. 42, Suppul. 1(1999).

* cited by examiner

*Primary Examiner*—Robert A. Wax
(74) *Attorney, Agent, or Firm*—Sughrue Mion, PLLC

(57) ABSTRACT

The present invention relates to a method for readily determining the binding site on plasma protein and binding displacement effect of a drug having binding affinity to plasma protein, and application of the method to clinical diagnosis. That is to say, the present invention provides a method for determining the binding site with plasma protein of a first drug, comprising reacting the first drug for which the binding site with plasma protein is to be determined, with a second drug of which the binding site with plasma protein is known and plasma protein, and determining the change in the ratio of the first drug freed due to the binding of the plasma protein with the second drug.

6 Claims, No Drawings

METHOD OF MEASURING BINDING SITE ON PLASMA PROTEIN OF PLASMA PROTEIN-BINDING DRUG AND METHOD OF MEASURING PLASMA PROTEIN MUTATION

TECHNICAL FIELD

This is a National Stage Application of International Application No. PCT/JP03/13572 filed Oct. 23, 2003.

The present invention relates to a method for readily determining the binding site on plasma protein and binding displacement effect of a drug having binding affinity to plasma protein, and application of the method to clinical diagnosis. More specifically, the present invention relates to a determining method which makes it possible to simultaneously determine the binding site on plasma protein and binding displacement effect of a drug from a small amount of sample, by adding to the plasma protein one or more drugs which may be labeled and have binding affinity to the plasma protein and for which the binding site is known, and determining the binding displacement effect of the drug which may be labeled from a resulting change in the ratio of the free drug to be assessed, in the determination of the binding site on plasma protein of a drug having binding affinity to plasma protein and binding displacement effect of the drug; and application thereof to clinical diagnosis.

BACKGROUND ART

Generally, a drug administered for the purpose of medical treatment or diagnosis once goes through the systemic blood circulation and then takes the method of absorption, distribution, metabolism, excretion and the like. In the method of absorption and distribution, the drug moves in the flow of the blood and migrates in each of the intravascular, interstice and intracellular spaces by diffusion and transportation of a free drug in a state not bound to protein, and finally the drug arrives at the active site of the target. When the migration of the drug reaches a steady state, the concentration of the free drug in each space becomes uniform, and the whole pattern of the drug concentration depends on the binding level to proteins and the like.

In this way, the drug exists in vivo partially and reversibly binding to a biopolymer such as a plasma protein or the like in accordance with the property thereof. Since the drugs permeable through capillary wall or cell membrane are unbound drugs in general, the drugs which may act as active ingredients are free drugs being unbound to plasma protein, etc. and the migration to the active site of the target is greatly influenced by the binding level of the drugs to the plasma protein, etc. The binding between the plasma protein and the drug affects the distribution to focus part on which the drug should act and excretion thereof, therefore, it is required in the development of a drug to investigate whether the drug binds to the plasma protein or not and to measure the binding level when they bind together.

WO00/78352A describes a method of administrating a drug comprising administrating the first drug having binding affinity to a plasma protein and administrating the second drug having binding affinity to the plasma protein in common with the first drug and thereby making it possible to regulate the binding of the first drug to the plasma protein as well as a pharmaceutical preparation therefor. That is, this WO publication describes that the administration of the second drug simultaneously with or before or after the administration of the first drug makes it possible to control the binding of the first drug to the plasma protein and to increase or decrease the concentration of the first drug freed in the blood.

For example, 99m-technetium labeled mercaptoacetylg-lycylglycylglycine ($^{99m}$Tc-MAG$_3$) is efficiently excreted into urine by renal tubular secretion in the kidney, and is a widely used radioactive pharmaceutical substance for use in vivo for the purpose of diagnosis of kidney and urinary tract diseases. It is known that about 90% of $^{99m}$Tc-MAG$_3$ binds to plasma protein when used in the concentration of a diagnostic agent. WO00/78352A describes that when 99mTc-MAG$_3$ is used as the first drug, binding between 99mTc-MAG$_3$ and plasma protein is controlled by the administration of bucolome, cefazolin, valproic acid, etc., which is the second drug, the concentration of the free $^{99m}$Tc-MAG$_3$ can be raised (displacement effect) and as a result $^{99m}$Tc-MAG$_3$ can be more efficiently excreted into urine.

Japanese Patent Application No. 2002-267010 by the present inventors describes that if a preparation containing an active ingredient which has binding affinity to a plasma protein is administered simultaneously with or before or after the administration of another preparation containing an amino acid which has binding affinity to the plasma protein in common with the active ingredient, competitive displacement occurs at the binding site and the concentration of the free active ingredient increases (displacement effect) and therefore it can be expected to attain higher drug activity rather than administrating the preparation containing the active ingredient alone to the patient. On the contrary, when the binding of an active ingredient to the plasma protein is increased by the action of the preparation containing amino acid, the concentration of the free active ingredient decreases (reduction effect of free drug concentration) and therefore it can be expected to attain continuous appearance of pharmacological effect due to decreased clearance resulting from the low concentration of the free active ingredient in the blood maintained for a longer period of time.

In the meantime, it is expected that the displacement effect by the preparation containing the second drug or an amino acid as mentioned above may vary depending on the first drugs and the living body to be administered. Typical plasma protein to which a drug binds includes albumin and acid glycoprotein, and it has been revealed that each of them has two or more binding sites, respectively. For example, when the binding site of the first drug and the binding sites of the second drug are the same, the concentration of the first drug freed is expected to change a lot due to the displacement effects of the second drug, while the binding sites differ, the change of the concentration of the first drug freed due to this displacement effect is expected to be small. For this reason, when the displacement effect by the second drug is anticipated, it is necessary to investigate the binding site(s) on the plasma protein to the first and second drugs beforehand. This is because if it can be known beforehand to which site of two or more drug binding sites on plasma protein the drug binds, prediction of pharmacokinetics of the drug will become easier.

On the other hand, when there are mutation and the like in albumin and acid glycoprotein (typical plasma proteins) themselves, the above-mentioned displacement effect may be significantly influenced. If change arises in the proteinic binding site, it will cause changes in the binding to a drug.

However, no simple method for determining the binding site and the amount of binding of a drug and plasma protein has not been developed until now.

In order to determine the displacement effect of a drug, as is described in WO00/78352A, the first drug labeled with a radioactive nuclide and the second drug for displacement is mixed with plasma, the radioactivity of the whole mixed solution is measured and the radioactivity of the filtrate containing the drug which has not bound to the protein is measured after carrying out ultrafiltration just to compare the both. However, by this method, there were problems that whenever the first drug and the second drug were changed, the displacement effect of the second drug should be determined, and that, for this reason, so much blood had to be sampled from the critical patient for measurement, and, in addition, the measurement takes labor and time.

DISCLOSURE OF INVENTION

The present invention has been achieved in view of the above, and aims at providing a method of determining the binding site and the binding amount with plasma protein of a first drug, comprising determining the change in the free drug ratio of the first drug to be assessed for binding to plasma protein, using a second drug of which the binding site with plasma protein is known. In the present specification, the ratio of a free drug which has not bound to protein is referred to as free drug ratio.

The present invention also aims at providing a method of detecting mutation of plasma protein, comprising determining the ratio of a free drug of which the binding site and the binding amount with normal plasma protein are known, from a small amount of sample.

Furthermore, the present invention aims at providing a method of detecting mutation of plasma protein, comprising determining change in the ratio of a free drug of which the binding site with plasma protein is known.

The present invention provides a method of determining the binding site with plasma protein of a first drug, comprising reacting the first drug for which the binding site with plasma protein is to be determined, with a second drug of which the binding site with plasma protein is known and plasma protein, and determining the effect of adding the second drug to the binding of the plasma protein of the first drug, i.e., the change in the ratio of the first drug freed.

Furthermore, the present invention provides a method of determining the binding site with plasma protein of a first drug, comprising reacting the first drug for which the binding site with plasma protein is to be determined with two or more second drugs of which the binding sites with plasma protein are known and plasma protein, and determining the change in the ratio of the first drug freed resulting from the binding of the second drugs to the plasma protein; and a kit for carrying out the method.

Furthermore, the present invention provides a method of detecting mutation of a protein in the blood, comprising reacting a drug of which the binding site and the binding amount with normal plasma protein are known with plasma protein, and determining the change in the ratio of the free drug; and a kit for carrying out the method.

Furthermore, the present invention provides a method of detecting mutation of a protein in the blood, comprising reacting a drug of which the binding site with plasma protein is known with plasma protein, and determining the change in the ratio of the free drug over time; and a kit for carrying out the method.

According to the method of the present invention, it is made possible to determine the binding site, the binding force and the binding amount with plasma protein of a certain drug, and therefore it is made possible to select a drug having a desired plasma protein binding profile from the group of a lot of candidate drugs. Moreover, according to the method of the present invention, the mutation of the drug binding site on the plasma protein of a healthy person and a patient can be known. Furthermore, when the method of the present invention is used, an additive required for controlling the binding to plasma protein with an existing drug (increasing the binding or increasing the free drug ratio), i.e., a second drug which is a displacing drug, can be selected.

Therefore, the method of the present invention can provide an additive for improving the pharmacokinetics of an existing pharmaceutical product to be prescribed in the living body, and the present invention can greatly contribute to improvement in the prescription of an existing pharmaceutical product, or investigation for a pharmaceutical preparation improved in the validity.

According to the method of the present invention, it is made possible to select a displacing drug for controlling the effect of a drug simply by using a small amount of a sample, and to determine the abnormalities of the binding site simply by using a small amount of sample when mutation of plasma protein occurs and therefore, the present invention greatly contributes to drug medication.

BEST MODE FOR CARRYING OUT THE INVENTION

It can be supposed that when the second drug which has high binding affinity to the plasma protein in common with the first drug is administered simultaneous with or before or after the administration of the first drug which has binding affinity with plasma protein, displacement occurs at the binding site and higher concentration of the first drug freed is resulted (displacement effect), and it can be expected that the higher drug activity can be obtained rather than the administration of the first drug alone. On the contrary, when the concentration of the first drug in the plasma protein is increased by the action of the second drug (reduction effect of free drug concentration), it can be expected to attain continuous appearance of pharmacological effect due to low concentration of the first drug freed in the blood maintained for a longer period of time.

As long as the purpose of administration is satisfied, such a first drug which has binding affinity to the plasma protein may be either a curative drug or diagnostic drug. In order to attain the above-mentioned displacement effect regardless of medical treatment or diagnostic purpose, the second drug is preferably selected from those having a competitive binding affinity to the same plasma protein as the first drug, and inhibiting the binding of the first drug to the plasma protein thereby increasing the amount of the first drug freed, or those having a binding site with the plasma protein in common with the first drug and having higher binding affinity. Conversely, in order to attain the reduction effect of free drug concentration, the object can be achieved by selecting from drugs which results in a higher effect to enhance the binding of the first drug to the plasma protein when it binds to plasma protein as the second drug.

Although there can be found no researches which clarify essential mechanism of such displacement effect and free drug concentration reduction effect of a drug, Japanese Patent Application No. 2002-267010 by the present inventors discloses examples in which binding of a drug to plasma protein is lowered (displacement effect) or enhanced (free drug concentration reduction effect) depending on the combination of the drugs. It is clearly desirable to determine the binding site at which the first and the second drugs bind with the plasma protein beforehand by the method of the present invention in order to attain such an effect by the combination of the first drug and the second drug. According to the determining method of the present invention, one or more second drugs can be used in combination for one first drug.

It does not matter whether the plasma protein in the determining method of the present invention derives from human or animal. Typical plasma proteins to which a drug binds include human serum albumin (HSA), $\alpha_1$-acidic glycoprotein (AGP), gamma globulin, lipoprotein, etc. and generally there are many drugs which bind to HSA and AGP.

HSA has binding sites such as site I, site II and site III. There are some drugs whose binding site on HSA has already been confirmed. The drugs having binding specificity to the site I include bucolome (5-n-butyl-1-cyclohexyl-2,4,6-trioxoperhydropyrimidine), cefazolin (7-(1-(H)-tetrazolylacetamido)-3-[2-(5-methyl-1,3,4-thiazolyl) thiomethyl]-3-cephem-4-carboxylate), phenylbutazone (1,2-diphenyl-3,5-dioxo-4-n-butyl-pyrazolidine), valproic acid (sodium 2-propylpentanoate), aspirin (2-acetoxybenzoic acid), salicylic acid (O-hydroxybenzoic acid), ceftriaxone (disodium (6R,7R)-7-(2-amino-4-thiazoyl)-2-methoxyiminoacetamide)-3-(2,5-dihydro-2-methyl-6-oxide-5-oxo-1,2,4-triazin-3-ylthiomethyl)-8-oxo-5-thia-1-azobicyclo[4.2.0] octo-2-ene-2-carboxylate), sulfamethizol (N-(5-methyl-1,3, 4-thiadiazol-2-yl)sulfanylamide), canrenoic acid (17-hydroxy-3-oxo-17 alpha-pregna-4,6-dien-21-carboxylate), dansyl-L-asparagine, etc. The drugs which specifically bind to the HSA site II include ibuprofen (2-(4-isobutylphenyl) propionic acid), nabumetone (4-(6-methoxy-2-naphthyl)-2-butanone (6-methoxy-2-naphthylacetic acid, which is a metabolite of nabumetone, shows binding specificity at the site II) and probenecid (4-(N,N-dipropylsulfamoyl)benzoic acid), etc. Further, etoposide ((5S,5aR,8aR, 9S)-9-[(4,6-O—(R)-ethylidene-β-D-glucopyranosyl)oxy]-5,8,8a,9-tetrahydro-5-(4-hydroxy-3,5-dimethoxyphenyl-isobenzofuro[5,6-f][1,3]benzodioxol-6(5aH)-one) also has binding specificity for HSA, though the binding site on the HSA has not been assigned.

The drugs having binding specificity to AGP include disopyramide (α-(2-diisopropylaminoethyl)-α-phenyl-2-pyridineacetamide), verapamil (α-{3-[(2-(3,4-dimethoxyphenyl)ethyl)-methylamino]propyl}-3,4-dimethoxy-α-(1-methylethyl)benzeneacetonitrile) and propranolol (1-isopropylamino-3-(1-naphthyloxy)-2-propanol), erythromycin, etc.

AGP has an acidic drug binding site (site A) and a basic drug binding site (site B) as binding sites. There are some drugs which have already been confirmed to bind with each site of AGP. The drug which has binding property to both the site A and the site B includes propranolol, and the drug which has binding property only to Site B includes verapamil.

These drugs must be used taking into consideration the influence on a living body, since they themselves have medicinal action.

In the meantime, Japanese Patent Application No. 2002-267010 describes a preparation for regulating the concentration of the active ingredient having binding affinity to plasma protein freed in the blood, characterized in that when the active ingredient having binding affinity to plasma protein is administered, a preparation containing one or more amino acids which have binding affinity to the plasma protein in common with the active ingredient is administered simultaneous with or before or after the administration of the active ingredient to control the binding of the active ingredient to plasma protein; and a method of administration therefor. This preparation containing one or more amino acids may be selected from, for example, tryptophan, aspartic acid, glycine, serine, leucine, methionine, phenylalanine, threonine, valine, proline, cysteine and alanine or the salt thereof and the derivatives thereof or the salt of these derivatives, etc. That is, these amino acids include amino acid derivatives into which substituent groups are introduced into amino acid molecules, such as N-acetyltryptophan and hydroxyphenylglycine, and the salts thereof. Here, two or more amino acids may be selected when, for example, the binding control of the active ingredient to two or more plasma proteins or two or more binding sites on a human serum albumin is expected or a synergistic effect is expected. Furthermore, when two or more amino acids are used, infusion containing two or more amino acids such as Proteamin 12X (registered trade-mark) and Kidmin (registered trade-mark) may be selected, or a preparation having the composition or containing the amount of ingredients equivalent to these infusions may be used. By using one or more amino acids for controlling the binding of the active ingredient to the plasma protein, the influence on the living body of the preparation for controlling the binding to the plasma protein itself can be lessened, and a preparation more suitable for practical administration can be provided.

Particularly, tryptophan is a displacement drug effective in the HSA site II and AGP, and while N-acetyltryptophan which is a derivative of tryptophan is a displacement drug effective in site II of HSA, it shows the free drug concentration reduction effect on AGP. Aspartic acid shows the displacement effect on AGP and hydroxyphenylglycine which is a derivative of glycine shows the free drug concentration reduction effect on HSA site II and AGP. On the other hand, amino acid infusion which is a mixture of amino acids like Proteamin 12X shows the displacement effect on both the binding sites of HSA site II and AGP and may be used as a general-purpose displacement drug.

Although the first drug or the second drug in the determining method of the present invention does not necessarily need to be labeled with a labeling substance, if the labeling of these drugs is carried out by various labeling substances such as a radioactive nuclide, a fluorescent substance and a dye, measurement of the displacement effect will become easy. Examples of the radioactive nuclides usable as a label include 3-hydrogen ($^{3}H$), 11-carbon ($^{11}C$), 14-carbon ($^{14}C$), 15-oxygen ($^{15}O$), 18-fluorine ($^{18}F$), 32-phosphorus ($^{32}P$), 59-iron ($^{59}Fe$), 67-copper ($^{67}Cu$), 67-gallium ($^{67}Ga$), 81m-krypton ($^{81m}Kr$), 81-rubidium ($^{81}Rb$), 89-strontium ($^{89}Sr$), 90-yttrium ($^{90}Y$), 99m-technetium ($^{99m}Tc$), 111-indium ($^{111}In$), 123-iodine ($^{123}I$), 125-iodine ($^{125}I$), 131-iodine ($^{131}I$), 133-xenon ($^{133}Xe$), 117m-tin ($^{117m}Sn$), 153-samarium ($^{153}Sm$), 186-rhenium ($^{186}Re$), 188-rhenium ($^{188}Re$), 201-thallium ($^{201}Tl$), 212-bismuth ($^{212}Bi$), 213-bismuth ($^{213}Bi$) and 211-astatine ($^{211}At$), and for diagnostic purpose, 18-fluorine ($^{18}F$), 99m-technetium ($^{99m}Tc$), 67-gallium ($^{67}Ga$), 111-indium ($^{111}In$), 123-iodine ($^{123}I$), 131-iodine ($^{131}I$), etc. are often used. In addition, labeling can also be carried out with 13-nitrogen ($^{13}N$), 22-sodium ($^{22}Na$), 35-sulfur ($^{35}S$), 40-potassium ($^{40}K$), 45-calcium ($^{45}Ca$), etc. which are nuclides widely used in a tracer experiment. In addition, if isotopes other than radioactive nuclides such as 2-hydrogen ($^{2}H$) are used, measurement by mass spectrometer is also possible. In the labeling using materials other than the radioactive nuclides, fluorescent substances such as fluorescein (3',6'-dihydroxyspiro[isobenzofuranyl(3H), 9'-(9H)xanthene]-3-one), fluorescein isothiocyanate, fluorescamine(4-phenylspiro[furan-2(3H), 1'(3'H)-isobenzofuran]-3,3'-dione) and dyes can also be used.

In addition, when two or more second drugs are used in the determining method of the present invention, labeling of the second drugs can be respectively carried out by the same or different labeling substance. Although separate measurement will become easier if a labeling is carried out with different labeling substances, the kind of labeling substance does not matter, since simultaneous separate measurement is possible even if the labeling substance is the same.

Needless to say, the first drug or the second drug in the method of the present invention can be separately measured simultaneously, without being labeled with a labeling substance. For example, the first drug, the second drug and the plasma protein in a mixed solution can be subjected to fraction measurement by high-performance liquid chromatography (HPLC).

According to the method of the present invention, a drug whose binding site and amount of binding with normal plasma protein are known is reacted with plasma protein, and change in the ratio of the free drug is measured and thereby the degree of the mutation of plasma protein can be determined. In addition, a drug whose binding site with plasma protein is known is reacted with plasma protein, and change in the ratio of the free drug is measured and a plasma protein variant can be detected. The plasma protein to be reacted may be present in any one of blood, plasma and serum.

Now the method of determining the plasma protein binding site of the first drug is described referring to Example 1. First, the first drug, for example, warfarin ($^{14}$C-WRF) is added to the serum 1 which was separated from a healthy adult, and as a control, the free drug ratio when further adding a physiological saline solution thereto (0.96 in Table 1) was determined. Here in this case, the binding site of warfarin is assumed to be unknown before the experiment. Next, the mixed solution of warfarin and serum 1 is divided into four, and to each of them, as the second drug, bucolome (BCL) which binds to HSA site I, ibuprofen (IPF) which binds to HSA site II, propranolol (PPL) which binds to site A and site B of AGP and verapamil (VPM) which mainly binds to AGP site B are added, and each free drug ratio is measured (2.83, 0.97, 1.00 and 1.06 in order in Table 1). The free drug ratio as a control in which a physiological saline solution is added is compared with these free drug ratios. Only when BCL is added, the free drug ratio is high, and the changes in the cases of adding IPF, PPL and VPM are slight. Here, since BCL has a binding site with HSA site I, it turns out that warfarin is a drug which also binds to the site I. Table 1 shows the results in the case using a healthy adult male serum, the similar results are also obtained with regard to the free drug ratio of control in Table 3 for the case in which human pooled serum is used.

When the first drug is changed to diazepam ($^{14}$C-DZP), only the ratio of IPF freed which has a binding site with the site II of HSA has increased 1.7 times compared with control, as similarly shown in Table 1. Accordingly, it is determined that diazepam is a drug having a binding ability to site II of HSA.

Although the cases in which the site to which the first drug binds is determined here were described, naturally the contrary is also possible. That is, when the fact that the binding site of warfarin is HSA site I is known, and in the case where $^{14}$C labeled warfarin is used as the second drug and BCL, IPF, PPL or VPM is used as the first drug, it can be judged that the first drug which binds to HSA site I among these first drugs is BCL.

Although the method of the present invention can determine the free drug ratio for every binding site for the labeled first drug, if two or more labeled second drugs which can be simultaneously determined are used, it can be judged to which site the first drug binds to by one operation. This is explained referring to Example 2.

In Example 2, simple determining method of the plasma protein binding site of a drug by simultaneous measurement of four nuclides is examined. As the first drug whose binding site with plasma protein is unknown, bucolome (BCL), ibuprofen (IPF), propranolol (PPL), verapamil (VPM) are used, and as the second drug, pertechnetium acid ($^{99m}$TcO$_4^-$) which binds to site I of human serum albumin (HSA), diazepam ($^{14}$C-DZP) which binds to site II of human serum albumin (HSA), propranolol ($^3$H-PPL) which binds to site A and site B of $\alpha_1$-acidic glycoprotein (AGP) and $^{125}$I-IMP which binds to site II of HSA and AGP are used. First, all of the above-mentioned second drugs were simultaneously added to normal human serum, a physiological saline solution was added and then radioactivity for each of them was measured, which was assumed as the free drug ratio of control. Subsequently, when the first drug, for example, ibuprofen, was added and the free drug ratio was measured, and as shown in Table 4, what changed remarkably compared with the free drug ratio of control was the ratio of $^{14}$C-DZP freed which binds to site II of HSA. Thus, it could be determined that the binding site of ibuprofen is the same as DZP, i.e., site II of HSA. The difference from Example 1 is that it is made possible to conduct determination at one operation, since the second drug labeled with four different labeling substances is used.

So far, examples in which the blood sample is normal are illustrated, but some blood of a patient may show different binding to plasma protein from that of a healthy subject. For this reason, it is desirable to grasp whether mutation is in the binding site of plasma protein of a patient before administration of a drug. Also in this case, the method of the present invention is applicable. That is, what is necessary is to determine the ratio of a free drug and free normal plasma protein beforehand, to react the drug with the plasma protein present in the patient blood, and to determine and compare the ratio of the free drug. When the drug is labeled with different radioactive nuclides like in Example 2, it can be known at one measurement in which site of two or more binding sites of plasma protein mutation has arisen. Hereafter, the present invention is illustrated by Examples 3 and 4.

In Example 3, the plasma protein binding site and the displacement effect of amino acid and amino acid infusion were measured using normal male serum. The free drug ratio when adding a physiological saline solution into normal male serum and adding pertechnetium acid which binds to site I of HSA, diazepam ($^{14}$C-DZP) which binds to site II of HSA, propranolol ($^3$H-PPL) which binds to site A and site B of $\alpha_1$-acidic glycoprotein (AGP) and $^{125}$I-IMP which binds to site II of HSA and AGP are shown in Table 5, which are 21.07, 1.50, 9.00 and 23.40, respectively.

On the other hand, in Example 4, the free drug ratios of control when adding a physiological saline solution to human serum 2 which is supposed to have mutation and adding these labeling drugs are determined. The free drug ratio was shown in Table 7 in the same order as in Table 5 and the free drug ratios of control were 21.08, 1.80, 21.40 and 27.23, respectively. Comparison of the two reveled that the free drug ratio is different by 2.3 or more times only for propranolol (PPL). Since PPL is a drug which binds to site A and site B of AGP, it is considered that serum 2 is a serum which has mutation in the binding site A and site B of AGP.

Moreover, if this method is performed with time, it is also possible to determine the mutation of the plasma protein in the same patient.

As above, the determining method of the present invention was illustrated. A kit for carrying out these determining methods can also be provided.

In determining a binding site with the plasma protein of the first drug, the kit may contain two or more the second drugs whose binding site with plasma protein is known as well as normal control serum. This kit can be constituted, if needed, as a kit which has an equipment which further enables ultrafiltration. The equipment which enables ultrafiltration may be composed of, for example, a container provided with a porous film on the bottom with the pore size sufficient to separate plasma and a pressure device which can apply pressure required for separation. When the plasma is put into this container and pressure is applied, the liquid ingredient excluding plasma protein is separated from the bottom of the container, and the radioactivity from the plasma portion and the radioactivity from the filtrate portion except plasma protein can be separated and measured.

In determining the degree of the mutation of the protein in plasma, the kit may contain a drug for which the binding site and the amount of binding with normal plasma protein are known as well as normal control serum. This kit can be similarly constituted, if needed, as a kit which has an equipment which further enables ultrafiltration. The plasma protein to be assessed is reacted with a drug for which the binding site and the amount of binding with normal plasma protein are known, the degree of the binding of the plasma protein and the drug is measured, and the binding site and the amount of binding between the drug and normal plasma protein is compared, thereby the existence of the mutation of the plasma protein binding site can be determined.

EXAMPLES

Hereafter, the present invention is illustrated by way of Examples in more detail, but the present invention is not limited to these Examples.

Example 1

Examination of the Simple Determining Method of the Plasma Protein Binding Site of the Drug by Simultaneous Measurement with Two Nuclides Warfarin ($^{14}C$ labeled substance: $^{14}C$-WRF was used in the experiment) which binds to site I of human serum albumin (HSA), diazepam ($^{14}C$ labeled substance: $^{14}C$-DZP was used in the experiment) which binds to site II of human serum albumin (HSA), propranolol ($^{3}H$ labeled substance: $^{3}H$-PPL was used in the experiment) which binds to acidic drug binding site A (site A) and basic drug binding site (site B) of $\alpha_1$-acidic glycoprotein (AGP), and verapamil ($^{3}H$ labeled substance: $^{3}H$-VPM was used in the experiment) which mainly binds to site B of AGP, are used to examine the displacement effect of each of the above-mentioned labeled drugs by the addition of a drug which has binding affinity to a particular plasma protein. As a drug which has binding affinity to a particular plasma protein, bucolome (BCL) which binds to HSA site I, ibuprofen (IPF) which binds to HSA site II, propranolol (PPL) which binds to site A and site B of AGP and verapamil (VPM) which mainly binds to AGP site B are used (test concentration: each 400 μM).

A serum (human serum 1:HSA=5.07 g/dL and AGP=72.0 mg/dL) separated from a healthy adult male blood and a commercial human pooled serum (product of Cosmo Bio Co., Ltd., Lot. No. 13768:HSA=4.40 g/dL and AGP=79.1 mg/dL) were diluted with 1/15M phosphate buffer solution (pH=7.4), so that the HSA concentration might be 500 μM. To 500 μL of this serum solution, 20 μL of the drug which has binding affinity to a particular plasma protein was added. At this time, each drug was dissolved in a physiological saline solution, and added in a serum solution so that the concentration might become test concentration. To the above-mentioned serum solution, 20 μL of a physiological saline solution was added instead of the solution of the drug and was used as a control solution. Then, a mixed solution of $^{14}C$-WRF ($3.7\times10^{-1}$ kBq/5 μL) and $^{3}H$-VPM ($9.25\times10^{-1}$ kBq/5 μL) or a mixed solution of $^{14}C$-DZP ($3.7\times10^{-1}$ kBq/5 μL) and $^{3}H$-PPL ($9.25\times10^{-1}$ kBq/5 μL) each containing two nuclides was added simultaneously to constitute a test solution.

20 μL each of the control solution and the test solutions was taken out as the sample before ultrafiltration. Then, 450 μL each of the control solution and the test solutions was taken out and put in an ultrafiltration equipment (Tosoh, Ultracent 10) and ultrafiltration was conducted by centrifuging under the condition of 3000 rpm, for 10 minutes using centrifuging machine RLX-135 (manufactured by TOMY). 20 μL of each filtrate was sampled after centrifugal operation, respectively, and used as the sample after ultrafiltration. To each sample before and after ultrafiltration a liquid scintillator (ACSII product of Amersham Biosciences) was added, and the radioactivity (cpm) of $^{14}C$ and $^{3}H$ was separately measured out with a liquid scintillation counter (LSC-5100, product of Aloka), and the free drug ratio of each test solution and the change of the free drug ratio by addition of a drug which has binding affinity to a particular plasma protein were obtained by the following formulas:

Free drug ratio (%)={radioactivity after ultrafiltration (cpm)/radioactivity before ultrafiltration (cpm)}×100

Change ratio (time)=free drug ratio of test solution (%)/free drug ratio of control solution (%)

The results by using the human serum 1 are shown and to Tables 1 and 2 and the results by using the human pooled serum are shown and to Tables 3 in which each of the free drug ratios of the control and test solutions is an average value of n=3.

In the human serum 1 shown in Table 1, by adding BCL which binds to HSA site I, only $^{14}C$-WRF, which is known to bind to HSA site I showed a significant displacement effect. Similarly, by the addition of IPF which binds to HSA site II, only $^{14}C$-DZP, which is known to bind to HSA site II was significantly displaced. On the other hand, by the addition of PPL and VPM which have binding affinity to AGP, each of $^{3}H$ labeled substance (3H-PPL and $^{3}H$-VPM) showed high displacement effect, but displacement effect to the binding site (site A and site B of AGP for $^{3}H$-PPL; site B of AGP for $^{3}H$-VPM) to which each of them corresponds became relatively high in accordance with difference of the affinity to the binding site on AGP. Therefore, it has been confirmed that this simultaneous determining method using two nuclides enables the binding site of the drug to the plasma protein to be readily determined, on the basis of the displacement effect of the labeled substance corresponding to the plasma protein binding site of the added drug. Furthermore, since the measurement can be carried out simultaneously from the same test serum by conducting separate measurement of radiation of two nuclides which are different in the displacement effect to two binding sites by using this method, measurement with a less amount of serum than before was attained.

Table 2 showed the results of the supplementary test using the same serum as Table 1, and almost perfect reproducibility was obtained and the high accuracy and high reliability of this determining method became clear.

Furthermore, although the degree of the displacement effect was different when human pooled serum was used (Table 3), the same result as the human serum 1 was obtained with regard to the response to the plasma protein binding sites, and therefore it was confirmed that this method can be applied general-purpose also in the serum having a different plasma protein composition.

TABLE 1

Displacement effect by binding site specific drugs on plasma protein binding of each labeled drug: Human serum 1

| | | | Labeled drug | | | |
|---|---|---|---|---|---|---|
| | | | $^{14}C$-WRF | $^{14}C$-DZP | $^3H$-PPL | $^3H$-VPM |
| | | | | Binding site | | |
| Drug/Main binding site | | | HSA Site I | HSA Site II | AGP Site A and B | AGP Site B |
| Free drug ratio of control (%) | | | 0.96 | 2.10 | 10.88 | 35.95 |
| BCL | HSA Site I | Free drug ratio (%) | 2.83 | 2.21 | 11.63 | 39.23 |
| | | Change ratio (time) | 2.96 | 1.06 | 1.07 | 1.09 |
| IPF | HSA Site II | Free drug ratio (%) | 0.97 | 3.57 | 10.47 | 36.56 |
| | | Change ratio (time) | 1.02 | 1.70 | 0.96 | 1.02 |
| PPL | AGP Site A and B | Free drug ratio (%) | 1.00 | 2.24 | 36.27 | 61.93 |
| | | Change ratio (time) | 1.04 | 1.07 | 3.33 | 1.72 |
| VPM | AGP Site B | Free drug ratio (%) | 1.06 | 2.31 | 33.50 | 65.37 |
| | | Change ratio (time) | 1.11 | 1.10 | 3.08 | 1.82 |

TABLE 2

Displacement effect by binding site specific drugs on plasma protein binding of each labeled drug: Supplementary test for human serum 1

| | | | Labeled drug | | | |
|---|---|---|---|---|---|---|
| | | | $^{14}C$-WRF | $^{14}C$-DZP | $^3H$-PPL | $^3H$-VPM |
| | | | | Binding site | | |
| Drug/Main binding site | | | HSA Site I | HSA Site II | AGP Site A and B | AGP Site B |
| Free drug ratio of control (%) | | | 0.97 | 2.07 | 10.98 | 36.22 |
| BCL | HSA Site I | Free drug ratio (%) | 2.75 | 2.24 | 11.55 | 39.41 |
| | | Change ratio (time) | 2.83 | 1.09 | 1.05 | 1.09 |
| IPF | HSA Site II | Free drug ratio (%) | 0.98 | 3.61 | 10.11 | 36.78 |
| | | Change ratio (time) | 1.01 | 1.75 | 0.92 | 1.02 |
| PPL | AGP Site A and B | Free drug ratio (%) | 0.97 | 2.18 | 36.24 | 61.63 |
| | | Change ratio (time) | 1.00 | 1.06 | 3.30 | 1.70 |
| VPM | AGP Site B | Free drug ratio (%) | 1.05 | 2.25 | 33.32 | 81.63 |
| | | Change ratio (time) | 1.09 | 1.09 | 3.03 | 2.25 |

TABLE 3

Displacement effect by binding site specific drugs on plasma protein binding of each labeled drug: Human pooled serum

| | | | Labeled drug | | | |
|---|---|---|---|---|---|---|
| | | | $^{14}C$-WRF | $^{14}C$-DZP | $^3H$-PPL | $^3H$-VPM |
| | | | | Binding site | | |
| Drug/Main binding site | | | HSA Site I | HSA Site II | AGP Site A and B | AGP Site B |
| Free drug ratio of control (%) | | | 0.89 | 2.62 | 11.82 | 36.22 |
| BCL | HSA Site I | Free drug ratio (%) | 2.58 | 2.98 | 12.41 | 36.67 |
| | | Change ratio (time) | 2.89 | 1.14 | 1.05 | 1.01 |
| IPF | HSA Site II | Free drug ratio (%) | 0.90 | 3.78 | 8.83 | 33.44 |
| | | Change ratio (time) | 1.01 | 1.44 | 0.75 | 0.92 |
| PPL | AGP Site A and B | Free drug ratio (%) | 0.91 | 2.76 | 34.28 | 52.14 |
| | | Change ratio (time) | 1.11 | 1.06 | 2.90 | 1.44 |
| VPM | AGP Site B | Free drug ratio (%) | 0.99 | 2.78 | 29.90 | 60.12 |
| | | Change ratio (time) | 1.11 | 1.06 | 2.53 | 1.66 |

Example 2

Examination of the Simple Determining Method of the Plasma Protein Binding Site of the Drug by Simultaneous Measurement with Four Nuclides Pertechnetium acid ($^{99m}TcO_4^-$) which binds to site I of human serum albumin (HSA), diazepam ($^{14}C$ labeled substance: $^{14}$C-DZP was used in the experiment) which binds to site II of human serum albumin (HSA), propranolol ($^3$H labeled substance: $^3$H-PPL was used in the experiment) which binds to acidic drug binding site A (site A) and basic drug binding site (site B) of $\alpha_1$-acidic glycoprotein (AGP), and $^{125}$I-IMP which binds to both the site II of HSA and AGP, are used to examine the displacement effect of each of the above-mentioned labeled drugs by the addition of a drug which has binding affinity to a particular plasma protein. As a drug which has binding affinity to a particular plasma protein, bucolome (BCL) which binds to HSA site I, ibuprofen (IPF) which binds to HSA site II, propranolol (PPL) which binds to site A and site B of AGP and verapamil (VPM) which mainly binds to AGP site B are used (test concentration: each 400 μM) as in Example 1.

In this experiment, a serum (human serum 1:HSA=5.07 g/dL and AGP=72.0 mg/dL) separated from a healthy adult male blood was diluted with 1/15M phosphate buffer solution (pH=7.4), so that the HSA concentration might be 500 μM. To 500 μL of this serum solution, a mixed solution of $^{99m}$TcO$_4^-$ (9.25×10$^{-2}$ kBq/5 μL), $^{14}$C-DZP, and (3.7×10$^{-1}$ kBq/5 μL), $^3$H-PPL (9.25×10$^{-1}$ kBq/5 μL) and $^{125}$I-IMP (1.85×10$^{-1}$ kBq/5 μL) containing four nuclides was added simultaneously, and sampling amount of 5 μL before and after ultrafiltration was taken. Physiological saline solution was added instead of the solution of the drug and was used as a control solution as in Example 1. Since the four above-mentioned nuclides are contained in the test solution, an autowell gamma counter (ARC-380, product of Aloka) was also used in addition to a liquid scintillation counter (LSC-5100, product of Aloka) for carrying out separate measurement of $^{99m}$Tc and $^{125}$I using an energy setup of γ-ray and after rectifying the influence by the γ-ray to $^3$H and $^{14}$C obtained from the counting ratio, the free drug ratio and change ratio after BCL, IPF, PPL and VPM are obtained. Results are shown in Table 4.

In the human serum 1 shown in Table 4, by adding BCL which binds to HSA site I, only $^{99m}$TcO$_4^-$, which is known to bind to HSA site I showed a significant displacement effect. Similarly, by the addition of IPF which binds to HSA site II, $^{14}$C-DZP and $^{125}$I-IMP, which are known to bind to HSA site II exhibited displacement effect. On the other hand, by the addition of PPL and VPM which have binding affinity to AGP, both of $^3$H-PPL and $^{125}$I-IMP, which have the same biding site, showed high displacement effect. Therefore, it has been confirmed that this simultaneous determining method using four nuclides also enables the binding site of the drug to the plasma protein to be readily determined, on the basis of the displacement effect of the labeled substance corresponding to the plasma protein binding site of the added drug. According to this method, since the measurement of the displacement effect for four binding sites can be carried out simultaneously from the same test serum by conducting separate measurement of radiation of four different nuclides and rectification, measurement of main drug binding sites was attained with a diluted serum of only 500 μL. Furthermore, it became possible to acquire information about many plasma protein binding from the same test serum by using simultaneously other possible labeling substance which can be subjected to separate measurement and rectification based on the same principle.

TABLE 4

Displacement effect by binding site specific drugs on plasma protein binding of each labeled drug: Human serum 1

| Drug/Main binding site | | | Labeled drug | | | |
|---|---|---|---|---|---|---|
| | | | $^{99m}$TcO$_4^-$ | $^{14}$C-DZP | $^3$H-PPL | $^{125}$I-IMP |
| | | | Binding site | | | |
| | | | HSA Site I | HSA Site II | AGP Site A and B | HSA Site II and AGP |
| Free drug ratio of control (%) | | | 21.07 | 1.50 | 9.00 | 23.40 |
| BCL | HSA Site I | Free drug ratio (%) | 25.14 | 1.50 | 9.00 | 23.75 |
| | | Change ratio (time) | 1.19 | 1.01 | 1.00 | 1.02 |
| IPF | HSA Site II | Free drug ratio (%) | 23.19 | 2.30 | 9.90 | 26.33 |
| | | Change ratio (time) | 1.10 | 1.55 | 1.09 | 1.13 |
| PPL | AGP Site A and B | Free drug ratio (%) | 22.70 | 1.60 | 29.30 | 30.60 |
| | | Change ratio (time) | 1.08 | 1.05 | 3.24 | 1.31 |
| VPM | AGP Site B | Free drug ratio (%) | 20.58 | 1.20 | 27.80 | 31.34 |
| | | Change ratio (time) | 0.98 | 0.80 | 3.08 | 1.34 |

Example 3

Examination of the Multi-Nuclides Simultaneous Measurement by the Plasma Protein Binding Site of a Drug and the Displacement Effect Thereby The simple determining method by two-nuclide simultaneous measurement in Example 1 and four-nuclide simultaneous measurement shown in Example 2 were used and plasma protein binding sites and displacement effects were examined for erythromycin (ETM) considered to be a candidate drug as the second drug, which has binding affinity to plasma protein in common with the first drug mentioned in WO00/78352, and the amino acid and amino acid infusion (hereinafter, displacement drug) which are mentioned in Japanese Patent Application No. 2002-267010. As amino acids, tryptophan (Trp), N-acetyltryptophan (NAT), alanine (Ala), aspartic acid (Asp) and hydroxyphenylglycine (HPG) (each test concentration:400 μM) and an amino acid infusion Proteamin 12X (PTA) (test concentration:1/100) were added in the serum solution.

A serum (human serum 1:HSA=5.07 g/dL and AGP=72.0 mg/dL) separated from a healthy adult male blood and a commercial human pooled serum (product of Cosmo Bio Co., Ltd., Lot. No. 13768:HSA=4.40 g/dL and AGP=79.1 mg/dL) were diluted with 1/15M phosphate buffer solution (pH=7.4), so that the HSA concentration might be 500 μM. Physiological saline solution was added instead of the solution of the displacement drug and was used as a control solution. The results in the case of using human serum 1 are shown in Table 5, and the results of human pooled serum are shown in Table 6.

ETM which is an antibiotic is a leading candidate drug as a displacement drug which can be safely administered, and it has been confirmed from the result (Table 6) of this determining method that it is an effective displacement drug for a drug which shows binding affinity to AGP.

As for amino acid and amino acid infusion, it has been revealed that Trp does not show a significant displacement effect for a drug which has affinity to site I of HSA but it is an effective displacement drug for a drug which has affinity to site II of HSA or AGP (Table 5). In addition, it has been confirmed that Trp also acts as an effective displacement drug to the drug which has affinity to both site II of HSA and AGP (Table 5). On the other hand, NAT which is a derivative of Trp is an effective displacement drug for a drug which has affinity to site II of HSA but it showed an effect to reduce the concentration to some extent of a free drug which has affinity to AGP. Asp does not show a significant displacement effect for a drug which has affinity to site I or II of HSA, but it is an effective displacement drug for a drug which has affinity to AGP and it has been revealed that Asp also acts as an effective displacement drug to the drug which has affinity to both site II of HSA and AGP in total. In addition, HPG which is a derivative of glycine showed an effect to reduce the concentration of a free drug which has affinity to site II of HSA or AGP. As shown above, it has been revealed that each amino acid respectively acts as a displacement drug having a binding site specificity, and as shown in the example of PTA (Table 5), amino acid infusion which is a mixture of amino acid shows displacement effect for each of site I and II and AGP, and showed a possibility that it can be use as a general-purpose displacement drug.

TABLE 5

Plasma protein binding site and displacement effect of each displacement drug in human serum 1: Four-nuclide simultaneous measurement

| | | Labeled drug | | | |
|---|---|---|---|---|---|
| | | $^{99m}TcO_4^-$ | $^{14}C$-DZP | $^3H$-PPL | $^{125}I$-IMP |
| | | Binding site | | | |
| Diplacement drug | | HSA Site I | HSA Site II | AGP Site A and B | HSA Site II and AGP |
| Free drug ratio of control (%) | | 21.07 | 1.50 | 9.00 | 23.40 |
| Trp | Free drug ratio (%) | 22.28 | 3.50 | 18.40 | 32.59 |
| | Change ratio (time) | 1.06 | 2.36 | 2.03 | 1.39 |
| Ala | Free drug ratio (%) | 22.03 | 1.40 | 13.50 | 27.57 |
| | Change ratio (time) | 1.05 | 0.98 | 1.49 | 1.18 |
| Asp | Free drug ratio (%) | 21.69 | 1.40 | 18.00 | 29.47 |
| | Change ratio (time) | 1.03 | 0.92 | 1.99 | 1.26 |
| PTA | Free drug ratio (%) | 23.20 | 2.30 | 14.20 | 32.08 |
| | Change ratio (time) | 1.10 | 1.54 | 1.57 | 1.37 |

TABLE 6

Plasma protein binding site and displacement effect of each displacement drug in human pooled serum: Two-nuclide simultaneous measure

| | | Labeled drug | | | |
|---|---|---|---|---|---|
| | | $^{99m}TcO_4^-$ | $^{14}C$-DZP | $^3H$-PPL | $^{125}I$-IMP |
| | | Binding site | | | |
| Diplacement drug | | HSA Site I | HSA Site II | AGP Site A and B | HSA Site II and AGP |
| Free drug ratio of control (%) | | 0.90 | 2.54 | 12.34 | 33.98 |
| ETM | Free drug ratio (%) | 0.88 | 2.67 | 23.79 | 54.78 |
| | Change ratio (time) | 0.99 | 1.04 | 1.93 | 1.61 |
| Trp | Free drug ratio (%) | 0.98 | 5.71 | 12.47 | 31.78 |
| | Change ratio (time) | 1.08 | 2.25 | 1.01 | 0.94 |
| NAT | Free drug ratio (%) | 0.97 | 3.08 | 11.54 | 34.19 |
| | Change ratio (time) | 1.07 | 1.21 | 0.94 | 1.01 |
| HPG | Free drug ratio (%) | 0.90 | 2.39 | 10.38 | 34.74 |
| | Change ratio (time) | 1.00 | 0.94 | 0.87 | 1.02 |

Example 4

Application of Plasma Protein Variant Diagnostic by Multi-Nuclide Simultaneous Measurement, and Monitoring of Plasma Protein Binding of the Drug in Variant Serum The simple determining method by four-nuclide simultaneous measurement shown in Example 2 has been used and applied to the judgment and diagnosis of the serum whose particular plasma protein is a variant. In addition, the possibility of monitoring the protein binding displacement effect of a drug in the serum was examined.

As a serum, a serum separated from an adult male blood in which AGP is a variant (human serum 2: HSA=4.88 g/dL and AGP=38.0 mg/dL) were diluted with 1/15M phosphate buffer solution (pH=7.4), so that the HSA concentration might be 500 μM.

As a drug which has binding affinity to a particular plasma protein, bucolome (BCL) which binds to HSA site I, ibuprofen (IPF) which binds to HSA site II, propranolol (PPL) which binds to site A and site B of AGP, and verapamil (VPM) which mainly binds to AGP site B, were used (test concentration: each 400 μM) to examine applicability for judging and diagnosing the mutation of AGP. Physiological saline solution was added instead of the solution of the drug and was used as a control solution.

Results are shown in Table 7.

In the meantime, as a displacement drug selected in Example 3, as amino acids, tryptophan (Trp), alanine (Ala) and aspartic acid (Asp) (each test concentration:400 μM) and an amino acid infusion Proteamin 12X (PTA) (test concentration:1/100) were added in the serum solution, and the monitoring of the plasma protein binding sites and displacement effect was carried. The results are shown in Table 8.

The human serum 2 is a serum in which AGP is considered to be a variant from the plasma protein binding profile of drug. Also in Table 7, when PPL and VPM which have binding affinity to AGP were added, the displacement effect of $^3$H-PPL which has the same binding site was lower as compared with other serum shown in Example 2, and the displacement effect on $^{125}$I-IMP was also little. On the other hand, $^{99m}$TcO$_4^-$ which binds to the site I of HSA showed the significant displacement effect by addition of BCL which binds to the site I of HSA. In addition, when IPF which binds to the site II of HSA was added, the displacement effect was observed for $^{14}$C-DZP which binds to the site II of HSA but it conversely showed biding enhancing action, i.e., free drug concentration reduction effect on $^{125}$I-IMP. Furthermore, when BCL and IPF each of which has binding affinity to these HSAs was added, binding with $^3$H-PPL and $^{125}$I-IMP which shows binding to AGP increased. Thus, it was shown that existence of mutation of the plasma protein contained in the serum can be diagnosed easily from the difference of the displacement effect by the addition of a drug which has binding affinity to a particular plasma protein and applying the multiple nuclide simultaneous determining method to clinic. According to this method, since the measurement of main drug binding sites was attained with a diluted serum of only 500 μL, it is apparent that the method is useful as a diagnostic method using the serum of the patient.

Furthermore, in the case that such a plasma protein has been mutated, there is a high possibility that even a usual administration causes critical side effects. In addition, when the second drug which has binding affinity to plasma protein in common with the first drug mentioned in WO00/78352A, and amino acids, amino acid infusion, etc. mentioned in Japanese Patent Application No. 2002-267010 are used in combination, it becomes important to carry out monitoring of the displacement effect in each serum. Table 8 shows the results of monitoring using the human serum 2 shown in Table 7. Although the displacement effect is completely different as compared with the results of Example 3 since the measurement of all the main drug binding sites can be attained with a diluted serum of only 500 μL, it is apparent that the method can be applied to monitoring of serum of each patient.

TABLE 7

Displacement effect on plasma protein binding of each labeled drug by four-nuclide simultaneous measurement: Human serum 2

| | | | Labeled drug | | | |
|---|---|---|---|---|---|---|
| | | | $^{99m}$TcO$_4^-$ | $^{14}$C-DZP | $^3$H-PPL | $^{125}$I-IMP |
| | | | Binding site | | | |
| Drug/Main binding site | | | HSA Site I | HSA Site II | AGP Site A and B | HSA Site II and AGP |
| Free drug ratio of control (%) | | | 21.08 | 1.80 | 21.40 | 27.23 |
| BCL | HSA Site I | Free drug ratio (%) | 27.42 | 1.90 | 18.40 | 25.72 |
| | | Change ratio (time) | 1.30 | 1.07 | 0.86 | 0.94 |
| IPF | HSA Site II | Free drug ratio (%) | 25.28 | 3.10 | 11.20 | 24.10 |
| | | Change ratio (time) | 1.20 | 1.77 | 0.52 | 0.89 |

TABLE 7-continued

Displacement effect on plasma protein binding of each labeled drug by four-nuclide simultaneous measurement: Human serum 2

| | | | Labeled drug | | | |
|---|---|---|---|---|---|---|
| | | | $^{99m}$TcO$_4^-$ | $^{14}$C-DZP | $^3$H-PPL | $^{125}$I-IMP |
| | | | Binding site | | | |
| Drug/Main binding site | | | HSA Site I | HSA Site II | AGP Site A and B | HSA Site II and AGP |
| PPL | AGP Site A and B | Free drug ratio (%) | 17.23 | 2.30 | 38.70 | 27.85 |
| | | Change ratio (time) | 0.82 | 1.32 | 1.81 | 1.02 |
| VPM | AGP Site B | Free drug ratio (%) | 20.42 | 1.90 | 34.80 | 30.52 |
| | | Change ratio (time) | 0.97 | 1.08 | 1.63 | 1.12 |

TABLE 8

Plasma protein binding site and displacement effect of each displacement drug by four-nuclide simultaneous measurement: Human serum 2

| | | Labeled drug | | | |
|---|---|---|---|---|---|
| | | $^{99m}$TcO$_4^-$ | $^{14}$C-DZP | $^3$H-PPL | $^{125}$I-IMP |
| | | Binding site | | | |
| Displacement drug | | HSA Site I | HSA Site II | AGP Site A and B | HSA Site II and AGP |
| Free drug ratio of control (%) | | 21.08 | 1.80 | 21.40 | 27.23 |
| Trp | Free drug ratio (%) | 22.66 | 3.50 | 13.10 | 30.42 |
| | Change ratio (time) | 1.07 | 2.00 | 0.61 | 1.12 |
| Ala | Free drug ratio (%) | 22.55 | 1.50 | 13.20 | 26.57 |
| | Change ratio (time) | 1.07 | 0.84 | 0.62 | 0.98 |
| Asp | Free drug ratio (%) | 19.17 | 1.70 | 12.90 | 26.75 |
| | Change ratio (time) | 0.91 | 0.99 | 0.60 | 0.98 |
| PTA | Free drug ratio (%) | 47.98 | 6.20 | 19.10 | 14.41 |
| | Change ratio (time) | 2.28 | 3.49 | 0.89 | 0.53 |

The invention claimed is:

1. A method for determining whether a first drug binds to a plasma protein at the same site as any of a second or more drugs for which the binding site is known, said method comprising:

mixing the first drug with the plasma protein and determining the ratio of free first drug to total first drug to give a first free first drug ratio;

mixing the second or more drugs with the first drug and the plasma protein and determining the ratio of free first drug to total first drug to give a second free first drug ratio; and determining the ratio of the first free first drug ratio to the second free first drug ratio to give a change ratio, thereby determining whether the first drug binds to the plasma protein at the same site as any of the second or more drugs for which the binding site is known.

2. The method according to claim 1 wherein the plasma protein is derived from human or animals.

3. The method according to claim 1 wherein the first drug is labeled with a radioactive nuclide, a fluorescent substance or a dye.

4. The method according to claim 1 wherein the plasma protein is serum albumin or acid glycoprotein, and the second or more drugs bind to different binding sites of the plasma protein.

5. The method according to claim 3 wherein the second or more drugs are labeled with the same or different substances respectively.

6. The method according to claim 5, wherein the second or more drugs are labeled with different radioactive nuclides respectively, and these different radioactive nuclides can be separately measured simultaneously.

* * * * *